(12) United States Patent
Aho et al.

(10) Patent No.: US 6,353,038 B1
(45) Date of Patent: Mar. 5, 2002

(54) PLASTIC BASED COMPOSITE AND ITS USE

(75) Inventors: Allan Aho, Turku; Jukka Seppälä, Helsinki; Antti Yli-Urpo, Littoinen; Jouni Heikkilä; Ilkka Kangasniemi, both of Turku, all of (FI)

(73) Assignees: Bioxid Oy, Turku; JVS-Polymers Oy, Helsinki, both of (FI)

( * ) Notice: Subject to any disclaimer, the term of this patent is extended or adjusted under 35 U.S.C. 154(b) by 0 days.

(21) Appl. No.: 09/446,630

(22) PCT Filed: Jul. 6, 1998

(86) PCT No.: PCT/FI98/00572

§ 371 Date: Feb. 23, 2000

§ 102(e) Date: Feb. 23, 2000

(87) PCT Pub. No.: WO99/02201

PCT Pub. Date: Jan. 21, 1999

(30) Foreign Application Priority Data

Jul. 8, 1997 (FI) .................................................. 972890

(51) Int. Cl.$^7$ ............................................. C08L 33/14
(52) U.S. Cl. ..................................................... 523/105
(58) Field of Search ......................................... 523/105

(56) References Cited

U.S. PATENT DOCUMENTS

| | | | |
|---|---|---|---|
| 4,595,713 A | | 6/1986 | St. John ...................... 523/105 |
| 4,645,503 A | | 2/1987 | Lin et al. ....................... 623/16 |
| 5,338,772 A | | 8/1994 | Bauer et al. .................. 523/115 |
| 5,433,751 A | | 7/1995 | Christel et al. ................ 623/16 |
| 5,552,454 A | * | 9/1996 | Kretschmann ............... 523/113 |
| 5,964,807 A | * | 10/1999 | Gan ............................ 623/17 |
| 5,981,619 A | * | 11/1999 | Shikinami ................... 523/113 |
| 6,027,742 A | * | 2/2000 | Lee ............................. 424/422 |
| 6,197,410 B1 | * | 3/2001 | Vallittu ..................... 428/292.1 |

FOREIGN PATENT DOCUMENTS

| | | |
|---|---|---|
| EP | 0 714 666 | 6/1996 |
| EP | 0 747 072 | 12/1996 |

* cited by examiner

Primary Examiner—Paul R. Michl
(74) Attorney, Agent, or Firm—James C. Lydon

(57) ABSTRACT

A composite intended for medical use, in particular surgical or therapeutic use, characterized in that it comprises a mixture of
  a thermoplastic component plasticizable within the temperature range $-10°\ldots +100°$ C., which is substantially made up of hydroxy acids and structural units derived from hydroxy acid derivatives and the molar mass of which is within the range 30,000–1,000,000 g/mol, and which degrades in the body typically within a period ranging from a few days to several years, and which in its solid state is a mechanically strong plastic or rubbery material, and
  a bioactive component, which is a bioactive glass or a bioactive xerogel,
such that the plasticized thermoplastic component remains moldable for a certain period even after the temperature of the composite has been lowered to a temperature which is considerably lower than the setting temperature of said thermoplastic component.

17 Claims, No Drawings

PLASTIC BASED COMPOSITE AND ITS USE

The invention relates to a composite which contains a plastic-based bioactive component and is intended for medical, in particular surgical or therapeutic, use.

BACKGROUND OF THE INVENTION AND STATE OF THE ART

To elucidate the background of the invention and the state of the art, the publications used, to which reference is made below, are to be viewed as being incorporated into the description of the invention below.

Previously known composites made up of a plastic component and a bioactive component include combinations of hydroxyapatite and methylmethacrylate (literature references (1)–(5)).

However, a thermoplastic, plasticizable at a relatively low temperature, has not been used as the plastic component in the known composites mentioned above.

OBJECT OF THE INVENTION

The object of the invention is to provide a novel composite which is intended for medical use, in particular surgical or therapeutic use, and which contains a thermoplastic component and can be machined and molded into a piece-like, coherent, shock-resistant and load-resistant form.

It is a particular object to provide a composite which can be plasticized at a relatively low temperature.

It is also an object of the invention to provide a composite which is moldable for a certain period even after its temperature has been lowered to a temperature below the setting temperature of the plastic component.

It is a further object of the invention in particular to provide a composite in which the biodegradability, plasticization temperature and setting rate of the plastic component can be controlled separately.

SUMMARY OF THE INVENTION

The characteristics of the invention are given in claim 1. A composite according to the invention is characterized in that it comprises

- a thermoplastic component, plasticizable within a temperature range of $-10°$ C. . . . $+100°$ C., which is substantially made up of hydroxy acids or structural units derived from hydroxy acid derivatives, which has a molar mass within a range of 10,000–1,000,000 g/mol, and which degrades in the body typically within a period ranging from a few days to several years, and which in its solid state is a mechanically strong plastic or rubbery material and
- a bioactive component, which is a bioactive glass, a bioactive xerogel, a bioactive ceramic material, or a bioactive glass ceramic material.

Preferred Embodiments and a Detailed Description of the Invention

The term "medical" is to be understood in the wide meaning of the word and thus also covers dental and veterinary applications.

Bioactive Component

By the bioactive component used in the composite according to the present invention is meant a material which reacts in the physiological conditions of the body. The bioactive component may have one or more of the following properties: bondable to tissues, bioresorbable, bondable/resorbable, releasing active agents, mineralizing, biocompatible, and antimicrobial. The bioactive component is a bioactive glass, a bioactive ceramic material, a bioactive glass ceramic material, coral or a coral-based product, or a bioactive xerogel. The concept of bioactivity is discussed in, for example, Heikkilä's doctoral dissertation (Ref. 1).

In a composite according to the invention, the bioactive component is present as particles separate one from another. The word "particle" here covers particles of different sizes and shapes, such as fibers, solid or porous pieces, rods, microparticles and glass beads.

The bioactive glasses described in references (1)–(5) can be mentioned as examples of suitable bioactive glasses.

Suitable bioactive ceramic materials include Ca phosphates, such as hydroxyapatite.

An especially suitable bioactive component is xerogel. By xerogel is meant a dried gel, which is described in the literature (9, 11). Silica xerogels are partly hydrolyzed oxides of silicon. Hydrolyzed oxide gels can be produced by the sol-gel process, which has been used for the production of ceramic and glass materials for many years.

The sol-gel process is based on the hydrolyzation of metal alkoxides and a subsequent polymerization of the metal hydroxides. As the polymerization reaction progresses, additional chains, rings and three-dimensional networks are formed, and a gel, made up of water, the alcohol of the alkoxy group and the gel itself, is formed. The sol may also contain other additives, such as acids or bases, which are used for the catalysis of the reaction. If the alcohol and the water are removed thereafter from the gel by washing and evaporation, a xerogel is obtained.

The polymerization of the remaining OH groups continues during the drying. The polymerization continues for a long time even after the gelation. This is called aging. The further the polymerization proceeds, the more stable the gel or xerogel becomes. At room temperature, however, the polymerization will in fact stop after an ageing of a few weeks, and the xerogel will not become completely inert. If the temperature is raised, the polymerization reaction can be accelerated, the gel becomes more stable and shrinkage occurs, and internal stresses appear in the xerogel to an increasing degree.

If the temperature is raised to a sufficiently high level (approx. $1000°$ C. for monolithic silica gels), the gel or xerogel becomes a pure oxide and no OH groups are left in the material. However, in the case of pure oxides, the dissolution reaction rate is very slow. If the oxides are added together with other ions, such as Na, K, Mg or Ca, the reaction rate can be greatly increased. By these methods, bioactive glasses have been developed, which can form a silica gel layer on their surface through an ion exchange reaction. The dissolution rate of these glasses is controlled by the composition and surface area of the glass. The glasses are melted at a temperature above $1000°$ C. Therefore it is not possible to add any organic compounds to the structure of the glass.

Sol-Gel glasses have been used, for example, as implant materials, in particular in bone implants (11). These materials do not dissolve completely. The material is formed at a high temperature, and organic compounds cannot be incorporated into its structure. Klein et al. described that when used as implants, silica gels sintered at a lower temperature caused a strong cell reaction in macrophages and in lymphocytes.

Plastic Component

The thermoplastic component used in the present invention, plasticizable within a temperature range of $-10°$ C. . . . +100° C., may be to a varying degree biodegradable or even bioactive. The term "biodegradable" covers all plastics which are not inert. This group thus includes all bioresorbable plastics (degrading under the action of cells) and biodegradable plastics (degrading under the. effect of mere moisture). The use of the composite will determine whether it is expedient to select a plastic which. is biodegradable at a slower or a more rapid rate.

Biodegradable types of plastic are suitable for most of the uses of the composite according to the invention. A biodegradable plastic component disappears at the desired rate or is biologically nearly stable, and thus promotes the tissue contact and the desired tissue reaction of the bioactive component. The plastic of the composite thus keeps the particles of the bioactive component in place but does not necessarily prevent the bioactive material from coming into contact with tissue fluid. Since the plastic component gradually decomposes, the water of the tissue fluid comes through diffusion into contact with the bioactive component. Likewise, ions and any active additives released from the bioactive material can become diffused through the plastic and affect their surroundings. The surrounding and/or contact surface tissue grows, filling the void formed by the degradation of the plastic. Ultimately the plastic component decomposes completely and releases any possibly remaining bioactive component.

Alternatively, the plastic component may be nearly inert. A composite made up of a bioactive material and an inert plastic may, if the composite possibly breaks, repair itself in the physiological environment under the mineralizing affect of the bioactive component.

The suitable plasticization temperature (=setting temperature) of the plastic used is also determined according to the intended use of the composite. Plastics plasticizable within a temperature range of 5° C. . . . 70° C., preferably 37° C. . . . 55° C., are suited for most of the uses of the composite according to the present invention.

Especially suitable are plastics having a plasticization temperature in the vicinity of body temperature. The application of a product in plastic state will thus not cause thermal damage in the tissue. Also, additives, such as proteins, possibly admixed with the composite would remain undamaged in connection with the preparation and application of the product. If the product implanted in a tissue is required to be soft, it is possible to select a plastic component having a plasticization temperature some-what lower than body temperature. Such a product can be applied on a hardened form, whereafter it will soften in the tissue.

There are, however, applications in which a very low (down to −10° C.) setting temperature of the plastic is preferable. One example is a situation in which it is desired to apply a piece or a component therein at a low temperature, whereafter the said piece or component is activated as the temperature rises.

The plasticization temperature of the plastic component can be controlled very precisely, i.e. approx. ±1 . . . ±2° C.

Relatively slowly setting plastics, that is plastics which are moldable for a certain period, i.e. approx. 15 s . . . 30 min, preferably 1 . . . 10 min even after the temperature of the plastic has been lowered to a temperature considerably lower than its setting temperature, are especially suitable. By the term considerably lower is meant here several degrees Celsius, suitably approx. 10 . . . 15° C. If the plastic is of a slowly setting type such as this, it is not very critical even if its setting temperature is relatively high, i.e. above 55° C. The behavior described above is based on the slow mobility of large polymer molecules, in which case setting will occur for some time after the piece has cooled down.

Physiologically suitable types of plastic, plasticizable at a relatively low temperature, are previously known. Poly (ortho esters) (J. Heller, (6, 7)) can be mentioned as an example.

Structure of the Polymer

An especially suitable plastic is a copolymer which is based on structural units such as a hydroxy acid; a hydroxy acid derivative such as a cyclic ester of a hydroxy acid, i.e. lactone; or a cyclic carbonate, such as trimethyl carbonate. L-, D- and DL-lactic acids; L-, D- and DL-lactides; and epsilon-caprolactone are highly suitable structural units.

A plastic component which is a copolymer based on L-lactide and epsilon-caprolactone structural units is especially suitable for this use. The composition of the copolymer typically varies within the range $$\frac{\text{epsilon-caprolactone}}{L\text{-lactide}} = 2/98 \ldots 98/2$$

and the molar mass M of the copolymer is within the range 10,000 . . . 1,000,000 g/mol, suitably within the range 30,000 . . . 300,000 g/mol.

It is known that the polymerization of lactones and cyclic carbonates can be carried out by catalytic ring-opening polymerization. The catalyst used may be selected from many known options, and is typically an organometallic compound, such as tin(II) octoate or triethylaluminum. The control of the molar mass in polymerization of this type is based on an optimal selection of the polymerization temperature and. period. It is also possible to use so-called initiator compounds, some typical examples of which are multivalent alcohols such as glycerol. In the polymerization, the polymer chains grow, starting from the —OH groups of the initiator compound, in which case the molar mass-will be the lower the larger the amount of initiator present. It is possible to affect the shape of the forming molecule by the structure of the multivalent alcohol. Thus, for example, glycerol forms a comb-like molecule and pentaerythritol a star-like molecule. Polymerization which opens the lactone ring is described in, for example, literature reference The above-mentioned L-Lactide/epsilon-caprolactone copolymers based on hydroxy acid structural units are described in patent application No. FI 965067.

The control of the melting temperature of the plastic component, i.e. the polymer material, intended for the composite according to the invention is based on one hand on the selection of the monomer ratio in the initial substances and on the other hand on the control of the molar mass in the copolymerization. Both of these factors together affect the melting temperature of the copolymer obtained, and thus only certain combinations produce the desired result. An example of such a composition is a copolymer which contains poly-L-lactide 20% by weight and ϵ-caprolactone 80% by weight. If the molar mass of this copolymer is approx. 30,000 g/mol, typically a melting temperature of approx. 40° C. is obtained. If, however, the molar mass of the said copolymer is approx. 300,000 g/mol, a melting temperature of approx. 48° C. is obtained. By the control of the molar mass and the composition, a material with a melting temperature anywhere within the range −10° C. . . . +100° C. is obtained.

In many applications, it is desired that the implant material degrades in a controlled manner, or reversely, has mechanical properties that remain stable for at least a certain period. The first stage in the biodegradability of the polymers of the present type is hydrolysis which cuts down the polymer chains until the molecule size is at a level at which the enzymatic functions of the body are capable of converting the degradation products into compounds natural for the body.

In terms of the degradation rate, the hydrophilicity of the polymer is crucial. Thus, in the copolymers being discussed it is possible to control their hydrolytic degradation rate by controlling the monomer composition, and thereby also hydrophilicity, and this, in accordance with what has been stated above, directly affects the degradation of the material in the body.

In terms of the invention, it is essential that, if the composition of the material is solely or almost solely ε-caprolactone, the balance being, for example, L-lactide, DL-lactide, D-lactide or dimethyl carbonate, the polymer is almost stable in the body, or degrades very slowly, typically in the course of a number of years.

By the selection of the monomer composition and the simultaneous control of the average molar mass of the copolymer by means of the preparation parameters, it is possible to exploit the previously known good biocompatibility of polyhydroxy acids. On the other hand, a waxy version of the copolymer material according to the invention can be rendered very rapidly degradable by controlling of the average molar mass and the monomer composition, as presented above. In this case the degradation period in the body is typically from a few days to a few weeks.

The degradation rate of a copolymer which contains poly-L-lactide and ε-caprolactone can be controlled by means of the composition, so that when the lactide content is above 60% by weight, the polymer degrades within a period of less than one month and when the lactide content is below 20% by weight the degradation period is more than half a year. The degradation rate can be adjusted steplessly between these values by the control of the composition.

The compression resistance of a plastic component in solid state is more than 10 Mpa and its tensile strength at break more than 10 Mpa. The material is plastic or rubbery.

Composite

The plastic component and/or the bioactive component of the composite according to the invention may also contain one or more additives. Examples which can be mentioned of such additives include the elements Ca, Na, P, B, Al, Zn, K, F, Si, Mg, Cl and Ti and their compounds such as oxides; drugs, proteins, proteoglycanes, sugars, growth factors, hormones, enzymes, collagen and antioxidants. It is, of course, the use of the composite that determines the selection of the additive or additives.

The composite according to the invention may form a dense or porous piece. The desired composite structure is obtained by the control of the ratio of the plastic component to the bioactive component. The mixing ratio of the plastic component to the bioactive component can be controlled within quite wide limits, i.e. the concentration of the bioactive component may vary within a range of 1 . . . 98% by weight of the composite. If the concentration of the bioactive component is very high, a composite structure is obtained in which the plastic component forms a binder between the particles of the bioactive component. In this case a rigid composite resembling a sugar lump is obtained. If the concentration of the bioactive component is lower, i.e. less than 60% by weight, a plastic-like composite is obtained which may be soft or resilient when so desired.

The composite may be, for example, a coating, membrane, net, thread, fiber, powder, or a piece such as a plate, a bead, a tube, a nail, a rod or an adhesive.

The composite according to the invention may also be prepared in connection with its use, immediately before it is being placed in a tissue (for example, a bone or a tooth). In this case the composite is prepared by "melting" the plastic component and the bioactive component together.

On the basis of the composite according to the invention, it is also possible to prepare a multi-layer composite, such as a multi-layer membrane, so that the plastic components of the different layers plasticize at different temperatures. A multi-layer composite may also be made up of different layers in which the biodegradability of the plastic components is different. The surface layer, or part of the surface layer (one side, one edge area) of an implant made from a multi-layer composite may thus be more rapidly or more slowly biodegradable than the deeper layers of the implant.

The composite according to the invention may also contain holes or channels. Optionally it is also possible to make so-called nutrition channels in the composite during an operation as the composite is being installed.

Applications

The composite according to the invention can be used for preparing products suited for various uses, some examples being the following groups: bone or cartilage applications, tooth and jaw applications, cartilage coatings and soft tissue applications. Bone applications include, for example, bone or cartilage filling material, a product intended for repairing long bones, a plate for repairing the back of the eye or facial bones, bone cement, an adhesive for joining the product to a tissue or tissues, an implant coating, a piece for repairing the vertebral column, and a skull plate. Examples of tooth and jaw applications include temporary tooth filling material, temporary or permanent tooth root filling material, a parodontal product, a product to be installed in the cavity remaining after the extraction of a tooth, tooth cement, temporary tooth cement, temporary-crown material, tooth implant coating, occlusion index rail, surgical paste and template material, which may be, for example, a paste, ring or thread which is placed in the gingival pocket. A tissue guiding membrane or tube which is applicable to bone, tooth or soft tissue areas can also be mentioned. Further applications include protective cloth, wound dressing, adhesive tape, and a carrier for active agents and other biological structures (autogenic and allogenic bone) and for drugs.

The suitable composite or composites are selected according to the use of the final product.

As to the bioactive component, it can be noted that a composite based on bioactive glass is especially well suited for products which are hoped to promote mineralization (filling materials, tooth coatings, bone fillings, etc.) or which are hoped to form bone bonds for the reconstruction of bone deficiencies (bone fillings, bone cements, various implants, etc.). Composites based on a bioactive gel are especially well suited for final products the purpose of which is to release an active agent (for example, growth factor, hormone, cytostatic, etc.) for the treatment or prevention of a disease. A gel-based composite is also suitable for use in applications in which mineralization and the formation of bone bond are desirable. A gel-based composite is also suitable for the reinforcement of products (the use of gel fibers for the reinforcement of plastic, bone pins, bone nails and bone screws, membranes, tendon tissue, filling materials, bone fillers, etc.).

The plastic materials may be plastic or rubbery, and their areas of use are divided so that the plastic-like materials will be used mostly for filling purposes and the rubber-like ones mostly for release purposes. Of course, again all types of blends are possible, and the selection of the plastic is mostly determined on the basis of the mechanical requirements.

Bone filler material to be used for the treatment of a fracture of an articular condyle can be taken as an example material. In the treatment of a condyle fracture, the material is required to have sufficient mechanical strength in order for it to be able to support the cortical bone during the healing process. It must be moldable to fill a cavity in the porous bone. It must release inorganic and/or organic compounds promoting bone growth and mineralization for at least the duration of the healing process. Another example is the fracture of a long bone. In the treatment of the fracture, the material can be used for attaching (gluing) the bone ends in the fracture to each other. A third example is the attaching of small fractured fragments to the parent bone in, for example, a cartilage fracture.

Owing to the requirements presented above, the polymer matrix of a composite material must be plastic and melt to fluid state at approx. 42° C. Its degradation time should in general be approx. 1–6 months, depending on the target 1–3 years. The other component of the material must be a sol-gel-produced Ca,P-containing xerogel or a bioactive glass in a granular or fibrous form, in an amount of approx. 60–70% by weight of the material; this promotes the mineralization of the bone and the bonding of the bone to the material. A third component may be a sol-gel-produced xerogel which contains bone growth factor, promoting bone regeneration in a bone cavity or other bone deficiency.

The following table (Table 1) shows the requirements set on a composite according to the invention as a function of the drug form:

TABLE 1

|  | injectable | implantable | needle-like rod-like |
|---|---|---|---|
| polymer matrix | rubbery | plastic or rubbery | plastic |
| melting temperature | polymer melts at 45° C. viscosity low | melting temperature dependent on the drug | melting temperature dependent on the drug |
| gel | spray-dried beads | particle, fiber or monolith, depending on the shape of the piece | fiber |

PREPARATION EXAMPLES

Example 1

Preparation of a Matrix Polymer
Chemicals Used

The copolymers were prepared from ε-caprolactone monomer (ε-CL), >99% pure, Fluka Chemika No. 21510, batch 335334/1 794, and D,L-lactide (D,L-LA), Purac, batch DF386H. The catalyst used was tin(II) octoate (Stannous 2-Ethylhexanoate; SnOct), 95% pure, Sigma No. s-3252, batch 112H0248. The initiator used was glycerol, 99.5% pure, Fluka BioChemika No. 49767, batch 42489/2 1094.
Purification and Storage of the Chemicals Used There were molecular sieves (added on Feb. 15, 1995) present in the ε-caprolactone used, and the bottle was stored, protected from light, at +23° C.

The D,L-lactide was purified by recrystallization from toluene (b.p. 110° C.) at a mass ratio of 1:2 toluene/lactide. The lactide dissolved in hot toluene was poured from a round-bottomed flask into a beaker.. The lactide dissolved in toluene was allowed to recrystallize overnight at +23° C. After filtration (medium-rapid filter paper) the crystallized lactide was dried under a lowered pressure for 4 d at +40° C., the pressure being 4 mbar. The same steps were repeated. Thus, a twice recrystallized D,L-lactide, stored in an exsiccator in a refrigerator at +4° C., was used in the polymerization runs.

The stannous octoate and glycerol were used as such. They were stored protected from light at +23° C.

Preliminary Preparations for the Polymerization

On the previous evening the lactide to be used for the polymerization was placed in a vacuum chamber at +40° C. under a pressure of 4 mbar. The two-section reactor (volume approx. 0.7 l) required for the polymerization was assembled. In connection with the assembling of the reactor, the condition of the teflon seal of the reactor was checked. The proper closing of the upper and lower sections of the reactor was ensured by using a closing device made from steel wire. Tap grease was applied lightly to the inside upper surfaces of the ground joints of the reactor.
Polymerization The oil bath used for the heating of the reactor was adjusted to 140° C. The temperature of the oil varies during polymerization by 5° C. above and below the setting value. First, approx. 10 g of the lactide was weighed into a small beaker (precision 0.0001 g). The stannous octoate and the glycerol were weighed and pipetted over the lactide by using a Pasteur pipette. Thereafter the beaker with its contents was poured into the lower section of the reactor. The rest of the lactide was weighed by using another balance (precision 0.01 g). The ε-caprolactone was either poured or pipetted over the lactide.

A magnetic stirrer was added to the reactor before the closing of the reactor halves. The reactor was placed in a bath, and the stirring rate was set at 250 min$^{-1}$. The reactor was rinsed with argon (Aga, quality grade S, 99.99 %) for approx. 15 min. The argon was directed into the reactor via a glycerol lock. Finally the outer surface of the reactor was lined with a foil. The stirring rate was reset at 125 min$^{-1}$ when the forming copolymer began to become more viscous.
Copolymers Prepared and Their Analysis Table 2 shows a summary of the ε-caprolactone/D,L-lactide (ε-CL/D,L-LA) copolymerization runs and the results of the product analyses. In all of the polymerization runs the temperature was 140° C. and the polymerization time 24 h.

The molar mass values of the obtained copolymers, determined by gel permeation chromatography GPC, shown in Table 2, are the number-average molar mass $M_n$, the weight-average molar mass $M_w$, and polydispersity PD, obtained as the ratio $M_w/M_n$ of the above values. The same Table 2 shows the melting temperatures $T_m$, determined by differential scanning calorimetry (DSC), of the polymerization products obtained.

TABLE 2

| Example | ε-CL/ D,L-LA- ratio | SnOct- conc. mol/mol | Glycerol conc mol/mol | $\overline{M}_n$ 10$^{-3}$ g/mol | $\overline{M}_w$ 10$^{-3}$ g/mol | $T_m$ ° C. |
|---|---|---|---|---|---|---|
| 1 | 100/0 | 0,0001 | 0,005 | 45 | 60 | 56 |
| 2 | 80/20 | 0,0001 | 0,005 | 40 | 60 | 42 |
| 3 | 100/0 | 0,0001 | 0,25 | 4,3 | 5,2 | 35 |
| 4 | 60/40 | 0,0001 | 0,001 | 20 | 40 | 38 |

Properties of the Polymer

Table 2 shows typical product polymers and their properties.
GPC Determinations

In the determination of the molar mass values by means of GPC, the samples were prepared by dissolving 15 mg of the sample in 10 ml of chloroform. The columns used were columns of Polymer Laboratories Ltd, having a pore size of $10^2$–$10^5$ Å. The samples were analyzed by using an RI, i.e. refraction index, detector manufactured by waters, the run time being 55 min at a flow rate of 1 ml/min. For the determination of the molar masses of the samples, an experimental calibration curve plotted by means of the polystyrene standards (PS) of Polymer Laboratories Ltd was used. Since experimental a-values and K-values of the Mark-Houwink equation are not available for the copolymers, the molar masses in Table 2 are not the absolute molar masses of the samples but relative values, compared with the PS standards.

DSC Determinations

In the DSC determinations, a sample of 5–10 g was heated at a rate of 10° C./min in the calorimeter cell. In order to obtain the same thermal history for all of the samples, the samples were heated above their melting temperature, to a temperature above +80° C., and were cooled to approx. −50° C. The $T_m$ values, shown in Table 2, were registered from the curve of the second heating.

Example 2

Preparation of a Composite Material

An amount of 20 g of a polymer prepared according to Example 1 was taken. An amount of 20 g of a bioactive glass (type S53P4, reference 10) having an average particle size of 300 μm was taken. The components were poured into the Kneteter mixing head of a Brabender Co-Kneader apparatus, where the rotation speed was 50 rpm. The temperature of the Kneteter head had been set at 55° C., and the mixing time was 15 min, whereafter the mixing head was opened and the homogenized material was recovered in a molten state.

The final product obtained was a homogeneous composite material having a bioglass content of 50% by weight. The composite was stored in a gas-tight vessel under nitrogen shield gas.

The above embodiments of the invention are only examples of the implementation of the idea according to the invention. For a person skilled in the art it is clear that the various embodiments of the invention may vary within the claims presented below.

LITERATURE REFERENCES

1. Heikkilä, J., Bioactive glass as a bone substitute in experimental and clinical bone defects, doctoral dissertation. University of Turku 1996.
2. Aho, A.J. & Heikkilä, J. T., Bone substitutes and related materials in chemical orthopaedics in *Advances in Tissue Banking* (Vol. 1), Phillips, Y. O., Versen, R., Strong, M., Nather, A. (eds.), World Scientific 1997, pp. 73–107.
3. Hench, L. L., Bioactive glass and tissue regeneration, in *Bioceramics,* Kokubo et al. (eds.). Pergamon Press 1996, pp. 3–6.
4. Ikada, Y., Bone-related polymeric biomaterials, in *bioceramics,* Kokubo et al. (eds.). Pergamon Press 1996, pp. 15–18.
5. Bonfield, W., Composite Biomaterials, in *Bioceramics,* Kokubo et al., (eds.). Pergamon Press 1996, pp. 11–13.
6. Heller, J., Development of poly(ortho esters): a historical overview, *Biomaterials,* 11 (1990), 659–665.
7. Heller, J., Roshos, K. V., Duncan, R., Use of poly(ortho esters) in the controlled release of therapeutic agents, Macroimol. Chem., Macromol. Symp. 70/71 (1993), 163–171.
8. I Ylikangas, "The polymerization of epsilon-caprolactone with stannous catalysts", Polymer Technology Publications, Series No. 15, Helsinki University of Technology 1993, 1–23.
9. C Jeffrey Brinker & George W Scherer "Sol-Gel Science—The Physics and Chemistry of Sol-Gel Processing". Academic Press, Inc. San Diego, Calif. 92101, 1990.
10. Ö H Andersson & K H Karlsson "Corrosion of bioactive glass under various in vitro conditions". Advances in Biomaterials No. 8, Elsevier (Amsterdam) 1990.
11. C. P. A. T. Klein et al., Biomaterials (1995) 16:715–719.

What is claimed is:

1. A composite intended for medical use, in particular surgical or therapeutic use, characterized in that it comprises a mixture of a thermoplastic component plasticizable within the temperature range −10° . . . +100° C., which is substantially made up of hydroxy acids and structural units derived from hydroxy acid derivatives, and the molar mass of which is within the range 30,000–1,000,000 g/mol, and which degrades in the body typically within a period ranging from a few days to several years, and which in its solid state is a mechanically strong plastic or rubbery material, and a bioactive component, which is a bioactive glass or a bioactive xerogel, such that the plasticized thermoplastic component remains moldable for a certain period even after the temperature of the composite has been lowered to a temperature which is considerably lower than the setting temperature of said thermoplastic component.

2. The composite according to claim 1, characterized in that the plastic component is plasticizable within the temperature range 5° C. . . . 70° C., preferably within the temperature range 37° C. . . . 55° C.

3. The composite according to claim 1, characterized in that the plastic component is biodegradable in a controlled manner within the time range 1 week–3 years.

4. The composite according to claim 3, characterized in that the structural unit is an L-, D- or DL-lactic acid; an L-, D- or DL-lactide; or epsilon-caprolactone.

5. The composite according to claim 4, characterized in that the plastic component is a copolymer based on structural units of L-lactide and epsilon-caprolactone.

6. The composite according to claim 5, characterized in that the composition of the copolymer is within the range $$\frac{\text{epsilon-caprolactone}}{L\text{-lactide}} = 2/98 \ldots 98/2$$

7. The composite according to claim 6, characterized in that $$\frac{\text{epsilon-caprolactone}}{L\text{-lactide}} = 4:1$$

8. The composite according to claim 7, characterized in that the molar mass of the copolymer is approx. 30,000–300,000 g/mol.

9. The composite according to claim 1, characterized in that the bioactive component is present as separate particles in the composite.

10. The composite according to claim 9, characterized in that the separate particles are fibers, porous pieces, microparticles or glass beads.

11. The composite according to claim 1, characterized in that the plastic component and/or the bioactive component contains one or more additives.

12. The composite according to claim 1, characterized in that the plastic component and the bioactive component form a dense piece.

13. The composite according to claim 1, characterized in that the plastic component forms a porous piece.

14. A blend intended for the preparation of a composite according to claim 1, characterized in that the plastic component and the bioactive component in the blend are in powder form.

15. A coating, membrane, net, powder, fiber, thread, adhesive, or a piece such as a plate, bead, tube, nail or rod, prepared from the composite according to claim 1.

16. The composite of claim 1, wherein the plasticized thermoplastic component remains moldable for a certain period even after the temperature of the composite has been lowered to a temperature approximately 10 to 15° C. lower than the setting temperature of said thermoplastic component.

17. The composite of claim 1, wherein said certain period is from 15 seconds to 30 minutes.

* * * * *